United States Patent [19]

O'Connell et al.

[11] Patent Number: 4,571,388

[45] Date of Patent: Feb. 18, 1986

[54] DETECTION OF RETICULOCYTES

[75] Inventors: James P. O'Connell, 1909 White Plains Rd., Chapel Hill, N.C. 27514; Burton H. Sage, Jr., 8404 Lakewood Dr., Raleigh, N.C. 27612

[73] Assignee: Becton Dickinson and Company, Paramus, N.J.

[21] Appl. No.: 460,144

[22] Filed: Jan. 24, 1983

[51] Int. Cl.$^4$ ............................................. G01N 1/30
[52] U.S. Cl. ................................ 436/63; 250/416.2; 436/172

[58] Field of Search .................. 436/63, 94, 172, 800; 250/461.2; 356/39

[56] References Cited

U.S. PATENT DOCUMENTS 3,872,312  3/1975  Hirschfeld ..................... 250/461.2
4,325,706  4/1982  Gershman et al. ............... 356/39 X Primary Examiner—Barry S. Richman
Assistant Examiner—John Donofrio
Attorney, Agent, or Firm—Elliot M. Olstein

[57] ABSTRACT

Reticulocytes are stained with thioflavin T for detection in a flow cytometer.

7 Claims, No Drawings

DETECTION OF RETICULOCYTES

The present invention relates to the detection and enumeration of reticulocytes in a blood sample. This invention further relates to a fluorescent composition.

In many cases, there is a need to detect RNA or RNA containing substances. Thus, for example, reticulocytes are a substance known to contain RNA, and detection and enumeration of reticulocytes in a blood sample are of value to clinicians. The reticulocyte count of a blood sample is used as an indicator of erythropoietic activity, has diagnostic and prognostic value in acute hemorrhage and hemolytic anemia, and is a measure of response to iron, vitamin $B_{12}$ and folic acid therapy. As known in the art, reticulocytes are precursors to mature red blood cells, and hence the term reticulocyte embraces the evolution and development of the cell whereby a mature red blood cell is generated.

In the past, reticulocytes in a blood sample have been determined by both manual and automated methods by using appropriate stains such as new methylene blue (NMB), brilliant cresyl blue (BCB), acridine orange and pyronin Y.

Vital staining with the dye new methylene blue is considered to be the reference method for reticulocyte determinations, and in use this dye precipitates RNA. The method is manual, requires counting large numbers (for example, 500 to 1,000) of cells with a microscope, is slow, tedious, and subject to errors approaching 100%. New methylene blue is nonfluorescent and true precipitated RNA is often difficult to differentiate from precipitated stain.

Acridine orange has had some use in staining reticulocytes by both manual and automated procedures. Acridine orange also precipitates RNA, and this prevents quantitative estimates of RNA content because of potential quenching. Moreover, acridine orange does not lead to a diffuse fluorescent distribution of stained cells. Age profiles of the cells (based on RNA content being proportional to fluorescence) are not reliable. Acridine orange has a great affinity for the plastic tubing in flow cytometers which leads to increased background and lengthy procedures for removing the dye from the flow cytometer tubing. In addition, acridine orange stained cells are difficult to separate from the autofluorescent red cell peak, and the reticulocyte count is usually lower than that obtained with new methylene blue.

The use of pyronin Y requires prior fixation of the erythrocytes with formalin, is cumbersome, time consuming, and generally yields poor results. Moreover, pyronin Y has a very low quantum efficiency, leading to very low fluorescent signals.

Accordingly, there is need for new procedures for staining reticulocytes so as to provide a procedure for accurately determining reticulocytes in a blood sample.

In accordance with one aspect of the present invention, there is provided an improvement in a process for detecting reticulocytes wherein the reticulocytes are stained with dye thioflavin T (Basic Yellow #1, Color Index 49005).

In accordance with another aspect of the present invention, reticulocytes are detected in a flow cytometer after the reticulocytes have been stained with the dye thioflavin T.

In accordance with a further aspect of the present invention, there is provided a composition comprised of reticulocytes stained with the dye thioflavin T.

Applicant has found that thioflavin T is an effective dye for staining reticulocytes, and that the use of thioflavin T offers the further advantage that thioflavin T when unbound to ribonucleic acid provides little or no fluorescence, whereas thioflavin T when bound to ribonucleic acid in the reticulocytes is fluorescent.

In accordance with the present invention, when staining reticulocytes in a blood sample, the thioflavin T may be employed as an aqueous solution, and in particular as an isotonic saline solution, which may contain a minor amount of ethanol. The blood sample, which may be whole blood or mixed cells, is stained with the thioflavin T by mixing the blood sample with the isotonic solution of thioflavin T. Applicant has found that thioflavin T is a vital stain, and, accordingly, fixation is not required. Moreover, Applicant has found that by using thioflavin T as the stain, it is possible to detect and enumerate reticulocytes in a whole blood sample.

In using thioflavin T for the staining of reticulocytes, Applicant has found that this dye exhibits a strong absorption peak (unbound) at about 415 nm; however, in the unbound state, the dye does not provide either a detectable excitation or emission peak. When the thioflavin T stains the RNA in the reticulocytes, the optical properties thereof change dramatically. In particular, the absorption curve shifts to a longer wavelength, and the dye now exhibits strong fluorescence. The excitation maximum is at about 455 nm and the emission maximum is at about 485 nm, giving a Stokes shift of about 30 nm. As a result of the excitation peak of the bound thioflavin T being in the order of about 450 nm, in using the automatic flow cytometer, the light source may be a mercury lamp which has a major energy line at about 436 nm or an argon ion laser which has strong emission at 457 nm, or a helium-cadmium laser which has a strong emission at 441 nm. The lack of fluorescence of the thioflavin T dye when not bound to nucleic acid provides low backgrounds and allows an operator to select fluorescent threshold (or "gates") for an automatic flow cytometer by simply running an unstained control. Although excitation may be effected at other wavelengths, the thioflavin T stained reticulocytes are preferably excited at a wavelength from 420 nm to 480 nm.

Thioflavin T dye does not precipitate RNA, and as a result, the thioflavin T stained reticulocyte cells maintain a relatively homogeneous distribution of intracellular RNA, whereby there is a nearly linear relationship between the fluorescent signal measured for an individual reticulocyte and its RNA content. Clinically, this provides the physician with additional information beyond the reticulocyte count in that RNA content is a function of reticulocyte age. Accordingly, by using thioflavin T, a clinician has the ability to do reticulocyte age profiles as well as simple reticulocyte counts.

The use of thioflavin T for staining reticulocytes in a blood sample offers the further advantage that the fluorescent signals from the stained reticulocytes are well separated from those of the mature erythrocytes, whereby results can be directly read in an automatic flow cytometer without extensive data manipulation.

The stained reticulocytes, although preferably enumerated in an automatic flow cytometer, can also be counted by a manual procedure.

Automatic flow cytometers are well known in the art, and the present invention is not limited to the use of any particular flow cytometer. Thus, for example, thioflavin T stained reticulocytes may be detected and enumerated in the FACS IV ™ flow cytometer or the FACS Analyzer ™ flow cytometer, both sold by Becton Dickinson and Company. In using such automatic flow cytometers, fluorescent gates are set by use of an unstained control sample, and the fluorescent gates are then used on the stained sample.

In using an automatic flow cytometer, a whole blood sample may be effectively stained by mixing a 25 ul aliquot of thioflavin T in isotonic saline solution (0.2 mg/ml) with 10 ul of anticoagulated (with ethylene diamine tetraacetate) whole blood. The mixture is incubated for about 7 minutes at room temperature and the sample is diluted to 10 ml with isotonic saline solution. The diluted sample is then analyzed in the automatic flow cytometer. It is to be understood that the present invention is not limited to the hereinabove described staining procedure.

Applicant has found that use of an automatic flow cytometer for detection and enumeration of reticulocytes stained with thioflavin T provides results which closely correlate with results obtained by the known standard method for enumerating reticulocytes which employs new methylene blue (overall correlation coefficient of 0.93 for 47 samples run on both the FACS IV ™ and FACS Analyzer ™ flow cytometers). In using acridine orange as stain for 78 samples analyzed on the FACS IV ™ flow cytometer, the correlation coefficient was 0.75.

The use of thioflavin T stained reticulocytes in an automatic flow cytometer is particularly advantageous in that there are low fluorescent backgrounds and fluorescent gates may be easily selected by use of an unstained control. Moreover, there is no precipitation of intracellular reticulocyte RNA, whereby the cells need not be fixed. In addition, there is a linear relationship between the fluorescent signal for an individual reticulocyte, which provides information as to reticulocyte age.

Still another advantage of the present invention is that thioflavin T stained reticulocytes can be used in an automatic flow cytometer having lower sensitivities, e.g., one may use a mercury arc lamp as opposed to an argon laser.

Although *Flow Cytometry and Sorting*, pages 457-58, Edited by Melamed et al., John Wiley & Sons, describes the use of both acridine orange and thioflavin T for staining RNA of living cells, this publication does not indicate the possibility and/or feasibility of using thioflavin T as a stain for reticulocyte detection and enumeration in an automatic flow cytometer. In fact, as a result of the known low fluorescent efficiency of thioflavin T and the known low RNA content of reticulocytes, it was quite unexpected that thioflavin T could be effectively employed as a reticulocyte stain in an automatic flow cytometer and that the thioflavin T stain would be an improvement over an acridine orange stain which is known to have a fluorescent efficiency higher than thioflavin T.

Numerous modifications and variations of the present invention are possible in light of the above teachings, and, therefore, within the scope of the appended claims, the invention may be practiced otherwise than as particularly described.

What is claimed is:

1. A process for determining reticulocytes, comprising:
    staining reticulocytes with thioflavin T; and detecting the reticulocytes stained with thioflavin T.
2. The process of claim 1 wherein the detecting is effected in a flow cytometer.
3. The process of claim 2 wherein the thioflavin T stained reticulocytes are excited in the flow cytometer with light from a mercury arc lamp.
4. The process of claim 2 wherein the thioflavin T stained reticulocytes are excited in the flow cytometer with light from an argon ion laser.
5. The process of claim 2 wherein the thioflavin T stained reticulocytes are excited in the flow cytometer with light from a helium cadmium laser.
6. The process of claim 2 wherein the reticulocytes are present in a sample comprising whole blood.
7. The process of claim 2 wherein the reticulocytes are detected without fixation thereof.

* * * * *